(12) United States Patent  
Lyons

(10) Patent No.: US 6,171,606 B1  
(45) Date of Patent: Jan. 9, 2001

(54) FLEXIBLE THERAPEUTIC COPPER PATCH AND BRACE

(76) Inventor: Robert Lyons, 3913 NE. 21st La., Ocala, FL (US) 34470

( * ) Notice: Under 35 U.S.C. 154(b), the term of this patent shall be extended for 0 days.

(21) Appl. No.: 09/455,239

(22) Filed: Dec. 6, 1999

(51) Int. Cl.[7] .................................................. A01N 25/34
(52) U.S. Cl. ........................................... 424/402; 424/489
(58) Field of Search ............................ 424/402; 514/489, 514/499

(56) References Cited

U.S. PATENT DOCUMENTS

| 4,680,309 | * | 7/1987 | Maurer | 514/499 |
| 4,961,933 | | 10/1990 | Campos Pino | 424/630 |

FOREIGN PATENT DOCUMENTS

| 8505221 | * | 2/1996 | (CN) . |
| 0002341 | * | 6/1979 | (EP) . |
| 9204061 | * | 2/1993 | (ZA) . |

OTHER PUBLICATIONS

Text and graphics distributed electronically at the internet locatio "www.sabona.com" copies of which were submitted by applicant copies dated–Sep. 16, 1999.*

Text and graphics distributed electronically at the Internet location "www.sabona.com" copies of which are attached, regarding fabric supports including copper thread. (copies dated Sep. 16, 1999).

* cited by examiner

Primary Examiner—Thurman K. Page
Assistant Examiner—B. Fubara
(74) Attorney, Agent, or Firm—Sven W. Hanson

(57) ABSTRACT

A device for delivery of copper to the skin for therapeutic effect. A flexible patch is formed of a matrix material embedded or intermixed with copper particles. The matrix material is selected for its compatibility with the human skin. The patch is held in a conforming manner by a sleeve or other means to retain the patch against a targeted skin area. A contact area of the patch contains at least a portion of the copper particles, the surfaces of which are put in contact with the skin. Silicone is a preferred matrix material. The invention includes elastic braces including a copper containing patch and designed for encompassing a knee, wrist or other portion of the body.

12 Claims, 3 Drawing Sheets

FLEXIBLE THERAPEUTIC COPPER PATCH AND BRACE

BACKGROUND OF THE INVENTION

The present invention pertains to topical application of the naturally occurring element copper to the body for therapeutic effect. In particular the invention pertains to methods and devices for incorporating copper into braces and wraps to be placed about a human limb.

Topical or dermal application of metallic copper and copper complexes as a therapeutic treatment has been recognized for many years (see U.S. Pat. No. 4,680,309 to Maurer and U.S. Pat. No. 4,961,933 to Campos Pino). Application of copper to the skin is believed to provide minute amounts of copper to the body to provide an anti-inflammatory effect in the treatment of conditions such as arthritis. The anti-inflammatory effects of topical copper are also beneficial to individuals who suffer from sore muscles and joints due to athletic training or endeavor. In general, application of copper for this type of treatment is of two forms: either 1) elemental copper (or other forms) in a fluid medium rubbed directly onto the skin or 2) metallic copper maintained in contact on the skin for a prolonged time. Examples of the first form are provided in the above referenced patents. A well known example of the second form is the copper bracelet, which is a solid copper metal band worn about the wrist. Other methods of applying copper to the skin have been developed to provide particular advantages. One of these is a elastic fabric support worn tightly about a region of an arm or leg. Copper threads are woven through the fabric so as to be retained against the skin of the user when the support is worn. Typical of these products are those marketed by Sabona of London, Incorporated.

Prior methods and products for topical copper application have significant disadvantages for the user. Topical creams and ointments are inconvenient and messy and do not provide copper for a prolonged time period. Solid copper is difficult to apply due to the inherent rigid nature of solid metals. It is difficult to maintain a significant contact area between a solid and the complex contours of the human body. Although the woven support mentioned above is capable of maintaining solid copper in contact with the skin, the contact surface area is small due to the limited size and number of the copper threads.

SUMMARY OF THE INVENTION

The present invention is a method and device for applying and retaining copper on the skin in a form which is conformable to the contours of human limbs.

One object of the invention is a flexible patch compatible with human skin and in which copper particles have been imbedded or intermixed.

Another object of the invention is a fabric or elastic brace including a flexible patch containing copper particles.

A further object of the invention is a method of applying copper to the skin in which a flexible matrix material compatible with human skin is embedded with copper particles. The matrix is formed into a patch which is held in a conforming manner to the targeted skin region.

Solid metallic copper is rigid and not conformable to the human body. The objective of the present invention is to bring into contact with a skin region a sufficient amount of copper, in the form of a multitude of small pieces, to gain a therapeutic effect. The present invention is a patch, spot or area of conformable matrix material in which a large number of copper pieces or particles have been introduced to form a copper containing contact area. The conformable nature of the patch is essential to allowing the patch, and copper, to be molded into maximum contact with a targeted skin region. Although an individual copper particle's contact area may be small, the total contact area of copper over the patch is sufficient to provide the desired therapeutic effect. The matrix material used is also selected to be compatible with skin to ensure that irritation does not result from continuous contact. One example of an acceptable matrix material is substantially common silicon rubber.

One therapeutic patch according to the invention is formed by mixing copper powder with liquid uncured silicone. This mixture is then applied to form a thin patch on an elastic sleeve such as a common spandex athletic knee support. In use the sleeve acts as a means of biasing and conforming the flexible patch to the targeted skin area. Various amounts of copper may be used. The thickness of the patch is selected for durability and comfort.

The present invention has several advantages over prior methods as a means of delivering topical copper to the body. As discussed, it conforms well to the complex shapes of the human body, particularly as exists around joints such as the elbow and knee. A brace according to the present invention is durable and may be easily cleaned. The surface of the patch when eroded through use uncovers additional copper ensuring that effective copper surface is always present. The cushioning of the patch materials provide protection from incidental impact against the covered body parts. The invention includes methods of therapeutic treatment in which a conforming copper containing patch is retained against the skin. The benefit of the device as a protective device may also be provided by a patch containing no copper. A soft silicon patch provides protection from impact to the covered body region while the overlying sleeve retains the patch in place and protects abrasion protection to the patch.

The advantages and novel aspects of invention are best understood from the following drawings, detailed examples and claims.

DESCRIPTION OF THE PREFERRED EMBODIMENTS

Figure 1:
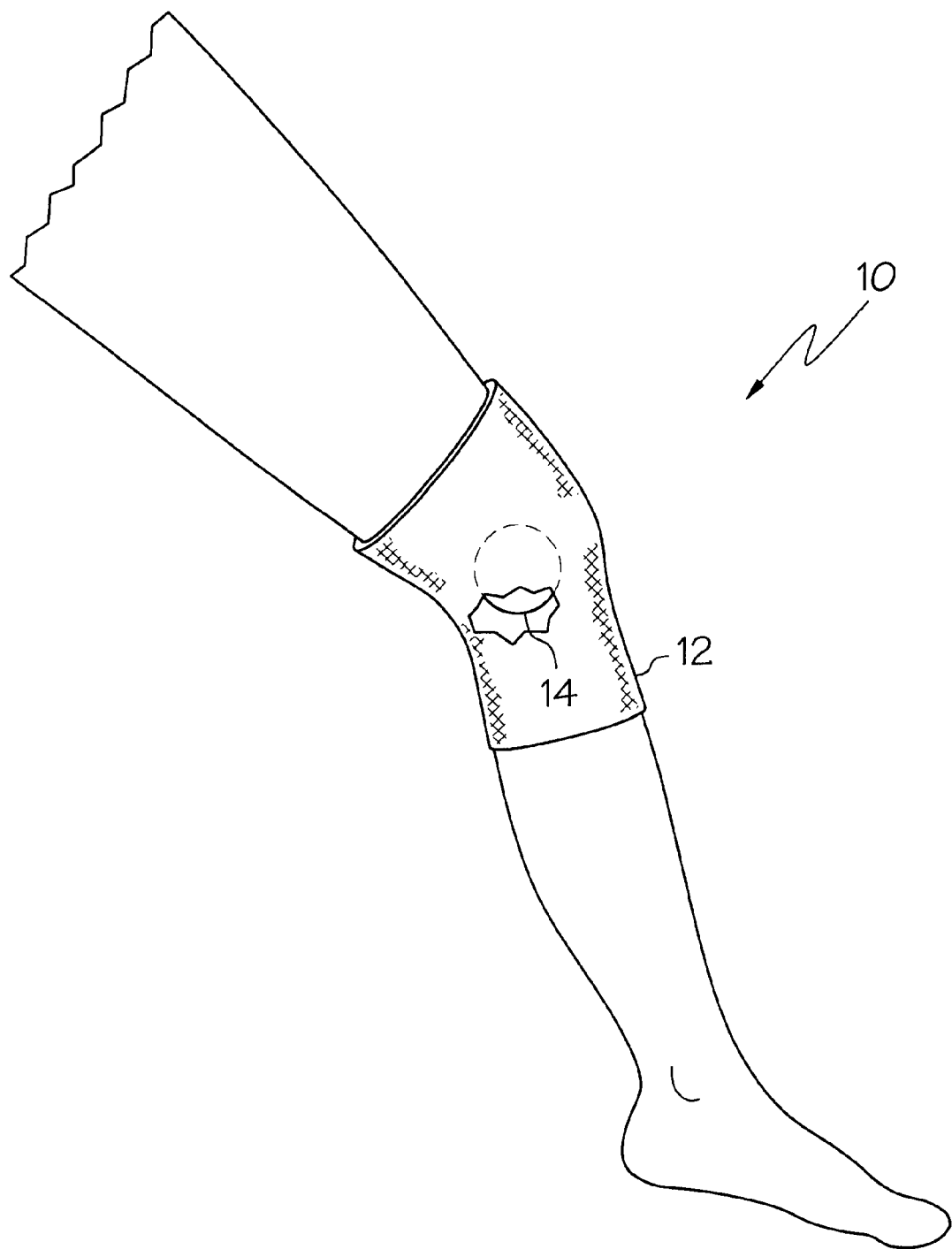
FIG. 1 is an illustration of knee brace in use incorporating a patch according to the present invention.
Figure 2:
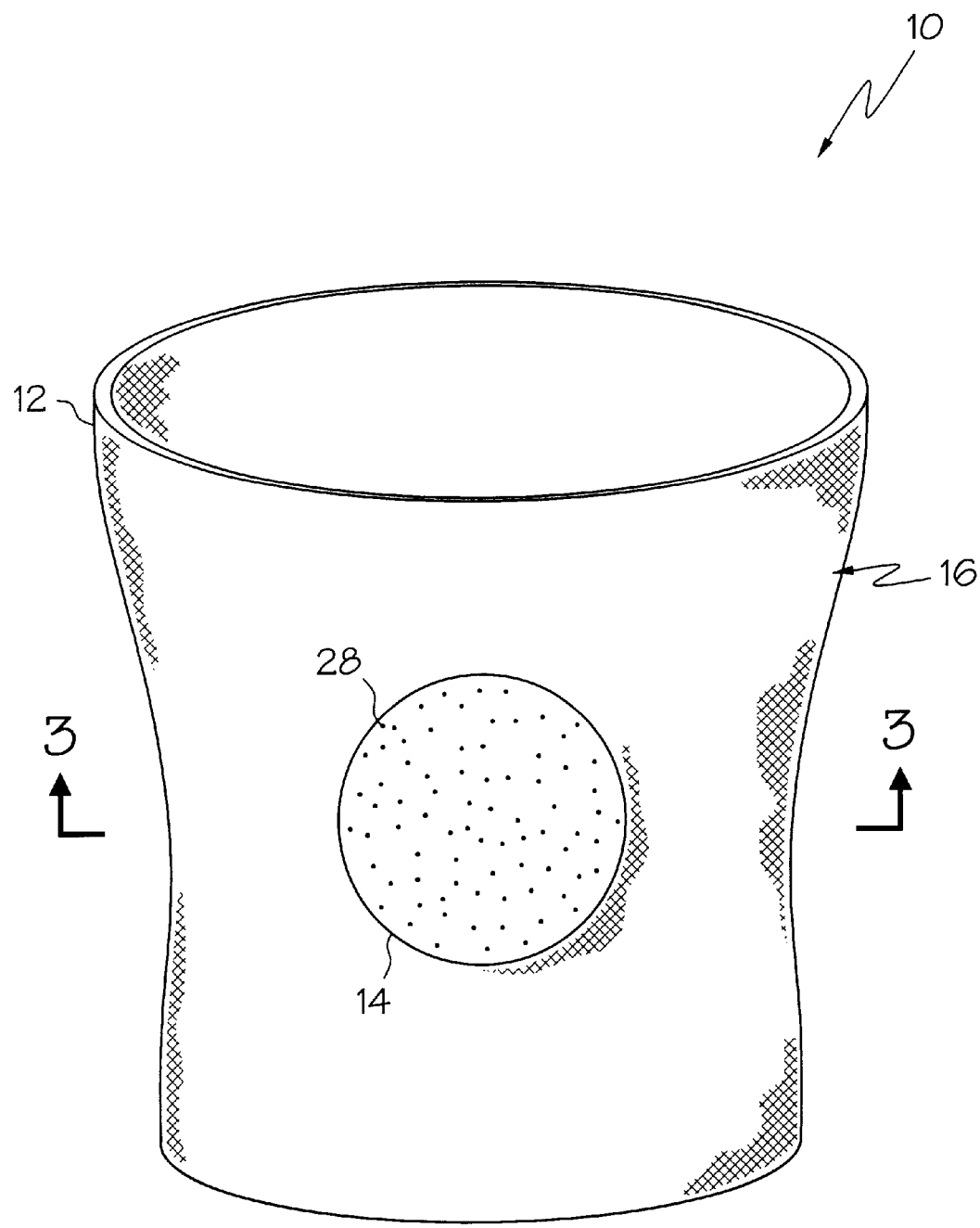
FIG. 2 depicts the brace of FIG. 1 that has been turned inside-out to make visible the patch.
Figure 3:
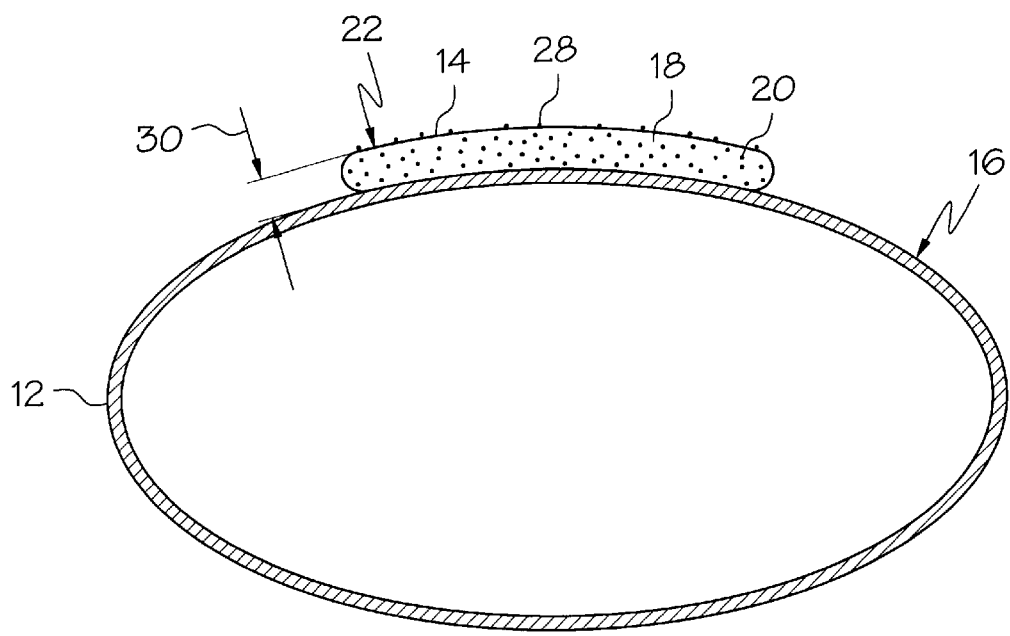
FIG. 3 is a cross-section of a copper containing path according to the present invention.

FIG. 1 depicts a brace 10 according to one embodiment of the present invention. The particular brace includes a sleeve 12 sized and shaped to fit around a human leg at the knee. The sleeve 12 is made of a flexible elastomeric fabric which, when stretched over the knee and released, draws snugly and conformingly about the contours of the knee. A patch 14 (exposed in the figure by cutting away a portion of the sleeve) is located on the inside of the sleeve 12 and is pressed against the knee by the elastic tension of the sleeve 12. Due to the flexible characteristics of the patch 14, it conforms to the contours of the knee beneath the sleeve 12 and patch 14. FIG. 2 depicts the same brace 10 turned inside-out to reveal the copper containing patch 14. The patch 14 is located on the inside surface 16 of the sleeve 12 so as to be aligned with a targeted skin area when the brace 10 is worn by a user. FIG. 3 is a cross-sectional view of the patch 14 on the sleeve 12 as shown in FIG. 2. The patch 14 consists of a matrix material 18 and copper particles 20. In the figures, the copper particles 20 are shown relatively large for the sake of clarity. The copper particles 20 are intermixed throughout the matrix 18. An exposed portion 28 of the copper particles 20 are exposed at a contact surface 22 of the patch. In use, when the patch 14 is drawn toward the skin, it is the contact surface 22 including the exposed copper particles 20 which contact and interact with the skin. The patch 14 includes sufficient exposed copper particles 20 so that an effective amount of copper may be delivered to the targeted skin area by contact.

The patch matrix 18 is preferably a silicone rubber (dimethylpolysiloxane). Silicone is known for its inertness and chemical stability and is used in many medical devices where contact with human tissue is required. One advantage of silicone's inertness is that a fabric brace having a silicone matrix patch may be simply cleaned in a standard clothes washing machine without significant deterioration. The patch has a thickness 30 preferably in the range of 0.030 to 0.060 inches (0.76 to 1.52 mm), measured from the surface of the sleeve 12 to the patch contact surface 22. This dimension range provides a durable patch having a desired level of comfort. Greater thicknesses may be effective in delivery of copper but do not provide additional benefit and result in a bulkier brace. Thinner patches may not have as great durability. The thickness 30 need not be constant over the patch 14 but may vary over the patch area by intent or incident to fabrication process. Thickness variation should not be so great as to prevent full contact of the patch 14 with the skin during use. Silicone can generally be produced in a great range of hardness. An acceptable hardness in the present case depends somewhat upon the particular patch thickness 30. The combination of hardness and thickness 30 must result in a patch flexibility that allows the patch to conform. Where the brace is designed to be worn over a relatively flat region of the body, such as the thigh, a high degree of flexibility may not be necessary. The appropriate hardness silicone will be easily identified by one skilled with such materials and the particular requirements. The copper containing patch preferably has a hardness in the range of 22 to 25 Durometer Shore A as determined by ASTM D2240.

In the embodiment of the figures, the patch 14 is an circular shaped region covering only a portion of the sleeve. The patch 14 may alternatively have any of an infinite variety of shapes. In other configurations, the shape may be modified to fit a particular targeted skin region or body part shape. The required size (total area) of the patch is dependent upon the extent of the targeted skin region and the total copper contact desired. In other embodiments, the patch 14 covers the entire inner surface of the sleeve 12. Such a brace design may be desired for use in situations where introduction of copper is desired at the entirety of a joint such as a wrist brace for a wrist joint. In other embodiments, a brace sleeve is provided with multiple patches to be directed at distinct separate targeted skin areas.

In the embodiment of the figure, the brace 10 is an essentially tubular sleeve 12. However, the copper containing patch of the present invention may be integrated into any of a great variety of braces, supports and wraps that are known for use on the body. These include braces, supports, and wraps for athletic, therapeutic and medical purposes and "brace" as used herein is meant to include all these generally.

While rigid braces or supports, such as a rigid splint, may be employed, a preferred brace includes a sleeve formed of a relatively light weight elastic fabric such as what is commonly known as spandex. Another effective support material is nylon covered neoprene foam rubber preferably of light gauge. While the embodiment shown in the figures has a tubular sleeve, the sleeve may be replaced by a non-tubular open wrap similar to what is commonly known as a ACE® bandage. Using such a wrap, the portion of the wrap having the patch is located over the targeted skin area and the wrap wound to provide the necessary tension and coverage. The essential function of the brace and sleeve is to act as a means of biasing and conforming the patch onto the targeted skin. While a tubular structure is preferred and has advantages, alternative structures can provide this function. A second function of the sleeve is to insulate the body portion under the brace to assist warming of the tissue; sleeve materials may be selected for this purpose as well.

Figure 4:
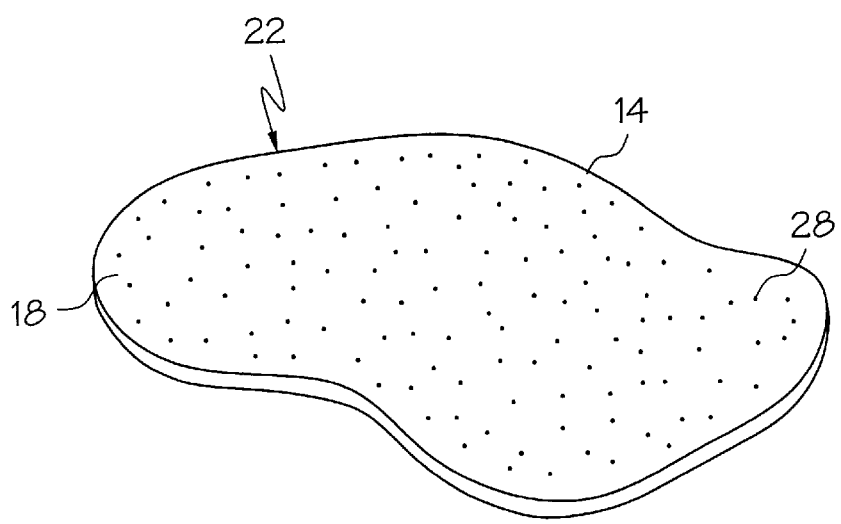
FIG. 4 depicts a conformable patch provided independent of a covering sleeve.

Silicone as a matrix material has an additional advantage at the time of forming the copper containing patch 14. Liquid silicone that cures at room temperature is available from a variety of sources. Some silicone products contain added chemicals and a silicone that is appropriate for contact with human tissue must be selected. One method of forming a patch is to mix liquid uncured silicone with the appropriate amount of copper particles, apply the mixture to a brace sleeve to the desired thickness and allow to cure. As well as capturing and providing a uniform distribution of the copper particles, the adhesive properties of silicone bond the cured patch to the brace sleeve. Alternatively, the copper and silicone mixture may be formed into a patch separate from a brace. Such a patch can be then be bonded to a sleeve with a second application of silicone or by other means. In alternative methods of use, a patch may be used as an article separate from the means of securing to the body. FIG. 4 depicts such a separate patch which is not bonded to a sleeve. A separated patch may be held loosely against the targeted skin and then bound in place by an support bandage or tubular sleeve. However, a brace with a formed integral patch on a sleeve is preferred for its convenience and durability. While pure silicone rubber is the preferred matrix material, other materials having similar properties may be used.

In alternative embodiments, the copper is contained in the matrix in a nonuniform distribution. In the above description, the copper particles are mixed relatively uniformly throughout the matrix. This structure has the advantage of providing an unchanging quantity of copper at the patch surface over time as the patch wears. Due to abrasion during use, the surface of the patch may slowly wear away. In a patch containing uniform copper throughout, additional copper is revealed as the surface matrix is removed. However, alternatively, the copper particles may be introduced to only a surface portion of the patch thickness, leaving the deeper regions of the patch without copper. This may be accomplished, in one method of fabrication, by applying the pure matrix material to a sleeve and subsequently applying copper particles to the exposed matrix surface to form a patch with copper particles bonded into the surface. In alternative embodiments, the copper particles may vary in density over the contact area of the patch. For example, the patch may include a region or spot at its center having a higher concentration of copper particles than in the surrounding areas of the patch. However, there is little benefit to such a construction and a uniform copper distribution is preferred. In any of the patch constructions discussed, other methods of forming familiar to those skill in the art, such as casting, may be employed.

The preferred construction of the present invention uses copper particles in the form of copper metal powder or filings. There are many sources of copper powder in various size particles. The particles should be small enough to be readily captured and retained by the matrix. Most typical sources of copper particles or filings are acceptable. A copper powder which has been used successfully is Caswell CCP9, a product supplied by Caswell Incorporated of Palmyra, New York, USA. Extremely large particles may become loosened and separate from the patch when the patch is flexed. Additionally, large particles will create hard spots against the skin resulting potentially in unacceptable discomfort. The copper particles may also be copper containing compounds and mixtures, such as copper oxides, which are capturable in a matrix such as silicone and which are compatible with contact with human skin.

A minimum effective amount of copper in topically treatment is uncertain as the exact mechanism for it therapeutic effect is not entirely understood. An effective amount is also dependent upon the particular condition treated and many physical and physiological characteristics of a particular user. In the present invention, to maximize effect, it is desirable to provide a maximum of copper for contact to the targeted skin. In silicone, copper has been successfully mixed at a ratio of 2 (two) parts copper powder (by volume) to 10 (ten) parts uncured liquid silicone. For the purposes of discussion and definition here, the subsequent patch is considered to be twenty (20) percent copper powder—although the actual final volume fraction of copper is slightly greater due to the interstitial air in dry powdered copper. A ratio of 2.5 parts copper powder to 10 parts liquid silicone is a practical maximum as greater proportions of copper are difficult to mix to a homogeneous mixture, the mixture being too dry.

In alternative embodiments, a silicone matrix patch is used to carry other effective agents. The characteristics of conformability and compatibility with the skin make this means appropriate for delivery of other topical treatments which are typically in solid form. In one alternative, magnetic elements are captured and retained in a patch according to the present invention for delivery to human skin. Treatment of particular human conditions by application of magnetic elements to the skin has received recent acceptance in the therapeutic field. In yet another embodiment, the silicone patch does not contain any effective agent such a copper. A brace utilizing a soft silicone patch according to the present invention provides protection from impact to a covered body region even if no effective agent is present. Generally, a silicone patch is somewhat hardened by the introduction of copper, so that a silicone patch without copper provides an even softer barrier to external forces. The combination of its highly conformable flexibility and its softness acts as an effective shield to the body.

The preceding discussion is provided as exemplary and not limiting of the embodiments within the scope of the invention. Other variations and embodiment of the claimed inventive concepts will be obvious to those skilled in the art. Adaptation or incorporation of alternative devices, materials and methods, existing and future is also contemplated. The intended scope of the invention is defined by the following claims.

I claim:

1. An improved device for topically applying copper to the human skin for therapeutic effect comprising:
   a flexible patch having a contact surface and comprising:
     a matrix compatible with continuous contact with skin,
     a plurality of copper particles secured in the matrix; and
   the contact surface comprising at least a portion of the copper particles.

2. The device of claim 1, further comprising:
   a brace for securing to a human limb, the patch being secured to the brace.

3. The device of claim 2, wherein:
   the brace comprises an elastic fabric sleeve, the patch secured to an inner surface of the sleeve.

4. The device of claim 3, wherein:
   the patch substantially covers the inner surface.

5. The device of claim 1, wherein:
   the matrix is substantially silicon rubber.

6. The device of claim 5, wherein:
   the copper particles are dispersed in the matrix.

7. The device of claim 6, wherein:
   the patch comprises 20 to 25 percent by volume copper powder.

8. The device of claim 7, wherein:
   the patch has a thickness of about 0.030 to 0.060 inches.

9. The device of claim 3, further comprising:
   a second flexible patch secured to the sleeve inner surface.

10. An improved device for topically applying copper comprising:
    a flexible patch comprising a matrix compatible with human skin and comprising copper particles; the patch having a contact surface comprising at least a portion of the copper particles; and
    means of biasing the patch in a conforming manner into contact with a human limb.

11. Method of applying copper topically to the human body, comprising:
    selecting a flexible matrix material compatible with human skin;
    introducing copper particles into the flexible matrix such that a surface of the matrix comprises a substantial portion of copper and forming a flexible patch; and
    pressing and retaining the patch surface against a skin area to maintain contact of the copper with the skin area.

12. The method of claim 11, wherein:
    the act of forming the matrix includes securing the patch to the inside of an elastic brace.

* * * * *